United States Patent [19]

Nemeth et al.

[11] Patent Number: 5,780,654
[45] Date of Patent: Jul. 14, 1998

[54] TITANOSTANNOSILICALITES: EPOXIDATION OF OLEFINS

[75] Inventors: Laszlo Nemeth, Palatine; Gregory J. Lewis, Mt. Prospect; Richard R. Rosin, Arlington Heights, all of Ill.

[73] Assignee: UOP LLC, Des Plaines, Ill.

[21] Appl. No.: 840,531

[22] Filed: Apr. 22, 1997

[51] Int. Cl.⁶ .................................................. C07D 301/12
[52] U.S. Cl. ................................................................ 549/531
[58] Field of Search ................................................. 549/531

[56] References Cited

U.S. PATENT DOCUMENTS

| | | | |
|---|---|---|---|
| 4,410,501 | 10/1983 | Taramasso et al. | 423/326 |
| 4,833,260 | 5/1989 | Neri et al. | 549/531 |
| 5,155,243 | 10/1992 | Fujiwa et al. | 549/531 |
| 5,463,090 | 10/1995 | Rodriquez et al. | 549/531 |
| 5,466,835 | 11/1995 | Nemeth et al. | 549/531 |
| 5,646,314 | 7/1997 | Crocco et al. | 549/531 |

OTHER PUBLICATIONS

Notari, B., *Innovation in Zeolite Materials Science*; Grobet, P.J. et al., Ed., Elsevier: Amsterdam, pp. 413–425, 1988.

A.J.H.P. van der Pol et al., *Applied Catalysis A: General*, 92 (1992), 93–130.

*Primary Examiner*—Ba K. Trinh
*Attorney, Agent, or Firm*—Thomas K. McBride; Frank S. Molinaro

[57] ABSTRACT

Titanostannosilicalites molecular sieves as new compositions of matter have been found to be very selective, active catalysts in the epoxidation of olefins by peroxides. Dilute hydrogen peroxide suffices to afford high yields of the epoxide with good selectivity. The sieves described within have a unit empirical formula, on an anhydrous basis of $(Ti_xSn_ySi_z)O_2$, where $0.0005<x<0.03$, $0.0001<y<0.01$, and $x+y+z=1$

17 Claims, No Drawings

TITANOSTANNOSILICALITES: EPOXIDATION OF OLEFINS

BACKGROUND OF THE INVENTION

One of the most challenging and formidable tasks in preparative organic chemistry is the selective functionalization of hydrocarbons. Once a functional group has been introduced, the chemist has a rich selection of tools to achieve further transformations and transpositions, but the initial barrier of introducing a functional group is determinative of further chemistry. Not only is it necessary that a given functionalization reaction proceeds in good yield, but it is necessary also that it proceeds with specificity. One of the most chemically attractive entry points to functionalization of hydrocarbons is the carbon—carbon double bond in alkenes and substituted alkenes, for the carbon—carbon double bond undergoes many reactions which introduce functional groups onto one or both of the carbons, and the double bond also activates an adjacent C—H bond (i.e., allylic hydrogen) to still other reactions. Among the chemical reactions of the carbon—carbon double bond that of epoxidation occupies a special niche, because epoxidation is virtually unique to the C=C linkage, because epoxidation proceeds with great specificity, and because the resulting epoxide is a functional group which controllably reacts with a wide range of reagents, schematically represented here as H—Y, to afford an equally wide range of difunctional materials according to the reaction,

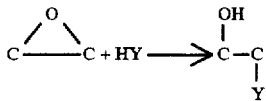

Although epoxidation may be performed with several different oxidizing agents, that variation of greatest interest here is one where the agent is a hydroperoxide. A commercial process uses tertiary butyl or ethylbenzene hydroperoxide in combination with 2% titania supported on silica to epoxidize propylene to propylene oxide with greater than 97% conversion of, for example, ethylbenzene hydroperoxide and selectivities to propylene oxide formation approaching 90%. See U.S. Pat. No. 3,642,833, 3,923,843, 4,021,454 and 4,367,342, all assigned to Shell Oil Company. More recently an Italian group has developed catalysts, referred to as titanium silicalites, where small amounts of framework silicon in silicalite are said to be replaced by titanium [Taramasso et al., U.S. Pat. No. 4,410,501], and has found such materials, conveniently designated as TS-1, to be effective in catalyzing the epoxidation of olefinic compounds by hydrogen peroxide in either the presence or absence of a solvent; U.S. Pat. No. 4,833,260. Subsequently this has been extended to the epoxidation of olefins with oxygen in air in the presence of a redox system of alkyl anthrahydroquinone and alkyl anthraquinone; EP 526,945.

Notari, B., *Innovation in Zeolite Materials Science*; Grobet, P. J. et al., Ed..; Elsevier: Amsterdam, pp. 422–424 has speculated that the observed catalytic activity both of titania supported on silica and TS-1 arises from the high dispersion of titanium atoms in a silica lattice, that is, active materials are characterized by Ti(IV) isolated by a long sequence of —O—Si—O-Si—. This conclusion was supported somewhat by the observation that when titania is supported on alumina, magnesia, or zirconia the resulting composite is inactive in epoxidation, and also is supported by the observation that catalyst activity increases as manifested by an increase in epoxide selectivity as the concentration of titania on silica decreases. Catalytic activity of TS-1 in the hydroxylation of phenol with $H_2O_2$ also has been shown to be dependent on particle size [A.J.H.P. van der Pol et al., *Appl. Catal.*, A92 (1992), 113–130] with particles in the 0.2–0.3 micron range being 10 times more active than those in the 5 micron range.

More recently Nemeth et al. have shown that particular mixtures of a titanosilicate and titania are demonstrably more active and more selective as a catalyst in the epoxidation of olefinic compounds than are prior art titanium-based catalysts which have been used in epoxidation and have linked the improved catalytic qualities to the particle size of both the titanosilicate and titania; U.S. Pat. No. 5,466,835.

In the quest for further improved oxidation catalysts we have recently investigated silicalites which incorporate both titanium and tin into the molecular sieve structure and have found that their incorporation at low levels is quite effective in modifying catalyst properties. There appears to be no reason to have expected this, for both activity and selectivity are increased concurrently. Additionally, we have determined that activity of titanostannosilicalites is quite dependent on particle size, as is the case for the titanosilicates alone. Furthermore, the titanostannosilicalites are quite stable catalysts; their activity is unchanged after several hundred hours on stream, and no tin leaching is observed.

Titanostannosilicalites have not been previously prepared, and our preparation methods are at once simple but capable of variation. We have observed that particle size is related to the synthesis method, and that crystallinity of the resulting material, as well as the degree of Ti and Sn incorporation, varies with crystallization temperature. We also have observed a correlation between epoxidation activity and crystallinity.

SUMMARY OF THE INVENTION

One purpose of this invention is to devise a facile, efficient process for the conversion of olefins generally to their epoxides in high yield and with great selectivity. One embodiment is the epoxidation of an olefinic compound by hydrogen peroxide using as a catalyst a titanostannosilicalite, especially where the average particle size is no greater than about 0.5 microns. In a more specific embodiment the epoxidation is conducted using hydrogen peroxide at a concentration no more than about 30 weight percent. In a more specific embodiment the epoxidation is effected with hydrogen peroxide at a concentration no more than about 15 weight percent and at a temperature no more than about 100° C. In yet another embodiment the olefinic compound is propylene. Another set of embodiments relate to the catalysts themselves and the preparation of our novel titanostannosilicalites. Other embodiments will become apparent from the ensuing description.

DESCRIPTION OF THE INVENTION

We have found that doubly substituted silicalites incorporating both tin and titanium, referred to here as titanostannosilicalites, are quite effective catalysts in the oxidation of olefins to their epoxides. Introduction of small amounts of tin(IV) into the framework of titanosilicalites such as TS-1 affords a crystalline molecular sieve with improved activity and selectivity in epoxidation of olefins using peroxides as the oxidizing agent relative to the singly substituted silicalites. The titanostannosilicalites show excellent catalytic stability; activity is unchanged even after several hundred hours of use, and the molecular sieve shows no propensity to change, particularly with respect to leaching of titanium or tin, with continued use. Hydrogen peroxide can be readily utilized as the hydroperoxide, even at concentrations as low as about 2 weight percent, and epoxidations often take place at a convenient rate at temperatures in the range of 0°–75° C., at least in the absence of reactive solvents.

The feedstock for the subject oxidation reaction contains olefinic compounds generally. The olefinic compound can be generally described according to the formula

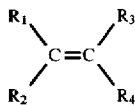

where $R_1$, $R_2$, $R_3$, and $R_4$ may be hydrogen, alkyl, aryl, cycloalkyl, aralkyl, carboxylic acid, carboalkoxy, a halogen, sulfonic acid, sulfonic acid ester, nitrile, sulfone, or ether group. The alkyl, cycloalkyl, arylalkyl, or aryl groups also may contain, e.g., a carboxylic acid grouping, carboxylic ester grouping, halogen, sulfonic acid or sulfonic ester grouping, nitrile, nitro, hydroxyl, ketone, anhydride, amino, hydroxyl, and ether groupings. As can be appreciated, our invention is applicable to an enormous diversity of olefinic compounds. In fact, the major criterion for a suitable feedstock is that it contain a non-aromatic carbon-carbon double bond.

One large group of olefinic compounds which may be used in the practice of our invention consists of the alkenes, especially those containing between about 2 and 20 carbon atoms. Such alkenes include ethylene, propylene, butene-1, butene-2, isobutylene, the pentenes, heptenes, hexenes, octenes, nonenes, decenes, undecenes, dodecenes, tridecenes, tetradecenes, pentadecenes, hexadecenes, heptadecenes, octadecenes, nonadecenes, and eicosene. Propylene, the butenes, pentenes, and hexenes (especially hexene-1) are particularly preferred in the practice of this invention. Dimers and trimers—and low-molecular weight oligomers generally—of the lower alkenes such as ethylene, propylene, and the butenes also are suitable olefinic compounds in the practice of this branch of the invention.

The cycloalkenes and the substituted cycloalkenes comprise another class of olefinic compounds which may be used in the practice of our invention. Suitable alkenes include cyclopentene, cyclohexene, cyclooctene, cycloheptene, cyclononene, and cyclodecene. Among other illustrative cyclic olefinic compounds are cyclooctadiene, dicyclopentadiene, methylenecyclopropane, methylenecyclopentane, vinylcyclohexene, methylcyclopentene, ethylcyclopentene, propylcyclopentene, methylcyclohexene, methylcycloheptene, and so forth.

Aryl substituted alkenes also may be used generally and include materials such as styrene, 1-phenyl-1-propene, 1-phenyl-2-propene, 2-phenyl-1-propene, the phenyl butenes, phenyl pentenes, phenyl hexenes, phenyl heptenes, divinylbenzene, indene, stilbene, and so forth.

The olefinic compounds which may be used in the practice of our invention may bear other functional groups, either at the olefinic carbons or, more generally, at a position other than the olefinic carbon. For example, alcohols and ethers thereof may be among the functionalized olefinic compounds used as a feedstock in our invention, including such materials as allyl alcohol, allyl methyl ether, allyl ethyl ether, 2-buten-1-ol, 3-buten-2-ol, 3-buten-1-ol, cinnamyl alcohol, alkyl and aryl ethers of the buten-1-ols, 2-methyl-2-propene-1-ol, alkyl ethers of the latter such as the methyl, ethyl, propyl, and butyl ethers, as well as such ethers as the benzyl and phenyl ethers thereof, all of which serve to illustrate the presence of an hydroxyl or ether group in the olefinic compound. Allyl alcohol and their ethers are particularly important inasmuch as the product, glycidol and glycidyl ethers, are important chemical intermediates.

Haloalkenes also may be used in the practice of this invention, particularly where the halogen is not on an olefinic carbon. For example, allyl chloride and allyl bromide afford as the epoxidation product epichlorohydrin and epibromohydrin, resp., both of which are important articles of commerce.

Olefinic carboxylic acids and their esters are another class of compounds which may be used in the practice of our invention and may be exemplified by such materials as acrylic acid, alpha-methacrylic acid, 2-butenoic acid, 3-butenoic acid, 2-pentenoic acid, 3-pentenoic acid, 4-pentenoic acid, 2-methyl-2-butenoic acid, 3-methyl-2-butenoic acid, 2-methyl-3-butenoic acid, and so forth. Other unsaturated acids of particular mention as olefinic compounds subject to epoxidation by the process of our invention include cinnamic acid, maleic acid, and fumaric acid, and the large class of unsaturated fatty acids and their esters, especially triglycerides, represented by acids such as linoleic acid, linolenic acid, oleic acid, ricinoleic acid, erucic acid, palmitoleic acid, and the like.

Other functional groups may be present in the olefinic compound, especially at the non-olefinic carbons, including such functional groups as the sulfonic acid grouping and their corresponding esters, the nitrile grouping, nitro and ether grouping. Dienes also may be used in epoxidation, especially butadiene. Except in unusual circumstances it must be recognized that dienes can be expected to undergo epoxidation at either C=C bond, hence the selectivity of the epoxidation of dienes can be expected to be low with respect to formation of an epoxide at but one point in the molecule. Consequently dienes, and polyenes more generally, are not favored among the olefinic compounds for this reaction, principally because of the complexity of the resulting reaction mixture. On the other hand, where selectivity of double bond epoxidation is unimportant polyenes may be readily numbered as among the suitable substrates in our invention.

The preferred epoxidizing agent of our invention is hydrogen peroxide, although organic hydroperoxides may be used but not necessarily with equivalent results. Among the organic hydroperoxides may be mentioned the alkyl hydroperoxides, especially tertiary butyl hydroperoxide and, to a lesser extent, the hydroperoxide of ethylbenzene. Peracids form another class of organic compounds furnishing the peroxide linkage and among these peracetic acid, trifluoroperacetic acid, and perbenzoic acid are the most commonly employed peracids.

The primary oxidizing agent which is used in the practice of this invention is hydrogen peroxide, especially as aqueous solutions. Thirty weight percent solutions of hydrogen peroxide in water have been standard in the prior art, but their disadvantage is that of cost. One important advantage of the process of our invention is that our catalysts are effective in bringing about epoxidation even with a feed containing dilute aqueous hydrogen peroxide as the oxidizing agent. Thus, feedstocks containing even 2 weight percent aqueous hydrogen peroxide solutions may be employed to convert the olefinic compounds present to their epoxide in yields in excess of 90% and with virtually 100% efficiency in utilization of hydrogen peroxide. In general, feedstocks containing as little as about 2% and as much as about 70 weight percent hydrogen peroxide may be used, although hydrogen peroxide concentrations of 2–15 weight percent are far more common, and concentrations of 2–10 weight percent are preferred. Where the olefinic compound is epoxidized under heterogeneous conditions, it behooves one to use as concentrated a hydrogen peroxide as is readily available, which generally translates to the use of a 30% hydrogen peroxide solution. Nonetheless, we need to emphasize again that the concentration of the hydrogen peroxide in the feedstock is not a controlling factor in the practice of our invention, that dilute hydrogen peroxide solutions can be readily employed, and that the concentration of hydrogen peroxide used is dictated by secondary factors extraneous to our invention itself.

We have found a new class of molecular sieves-the doubly substituted titanium-tin silicalites—to be particularly effective catalysts in the epoxidation of olefins. These titanostannosilicalites are novel compositions of matter with an empirical formula on an anhydrous basis,

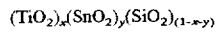
$$(TiO_2)_x(SnO_2)_y(SiO_2)_{(1-x-y)}$$

where x has values between 0.0005 and 0.03 and y has a value between 0.0001 and 0.03. An equivalent way to express the formula of our titanostannosilicalites is,

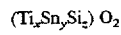
$$(Ti_xSn_ySi_z)\,O_2$$

where $0.005 \leq x \leq 0.03$, $0.0001 \leq y < 0.03$, and $x+y+z=1$.

In the molecular sieves of our invention, both titanium and tin are incorporated into the framework of the material. Incorporation of titanium into the framework is well known; we have shown the incorporation of tin into the framework of our new compositions of matter by showing that the tin concentrations at the surface and in the bulk of our material is identical, which is excellent supporting evidence for our hypothesis.

Although the titanostannosilicalites of our invention may be prepared in a broad variety of ways, during the course of developing the titanium-tin silicalites we have determined the critical synthesis parameters that lead to an active catalyst. The critical properties of the catalyst that have a bearing on the catalyst performance are the amount of Sn and Ti incorporation and the particle size. The critical synthesis variables that we found needed to be controlled were the reaction medium and the temperature. The optimal reaction medium was only a partly aqueous medium, especially alcohol-water mixtures, vs. purely aqueous. Aqueous reaction mixtures in which ammonia-stabilized colloidal silica was employed led to very large crystallites, 3–10 µ size, in contrast to aqueous-alcoholic preparations in which TEOS is employed, which tended to yield crystallites in the 0.1–0.2 µ range. This is probably due to the ethanol released by the TEOS during hydrolysis, which makes the solvent less polar than the pure aqueous systems. It also was possible to control the Ti incorporation using this solution as unincorporated Ti was soluble rather than precipitated on the surface as $TiO_2$, as is common in many gel preparations. Excess Sn was also soluble and not precipitated on the silicalite surface using these methods. The temperature was the critical factor in determining the amount of Ti and Sn incorporation. From 100° C. to 175° C., the incorporation of Ti and Sn increased; only at 175° C., when there was excess Ti, was the precipitation of $TiO_2$ observed. The incorporation of Ti and Sn as a function of temperature is shown in the Examples.

We have found that the crystallization temperature of the titanostannosilicalites is an important variable in the success of our invention. Not only does the incorporation of titanium and tin into the framework of the silicalite increase with increasing temperature, but the crystallinity of the resulting titanostannosilicalite also appears to be temperature dependent, going through a maximum in the 125°–150° C. region. This appears to coincide with the effectiveness of the titanostannosilicalite as a catalyst in propylene oxidation, as measured by the yield of propylene oxide. That is, it appears that oxidation activity, as measured by propylene oxide yield, correlates with molecular sieve crystallinity.

As has been previously observed for the titanosilicates, we have found that an average particle size (i.e., average particle diameter) of the titanostannosilicalite molecular sieve no more than about 0.5 microns is greatly preferred, and that sieves with an average particle size of no more than about 0.3 microns are still more highly preferred. When synthesis is performed in an aqueous alcoholic medium the requisite small particle size sieve results upon hydrothermal crystallization without added or special procedures, which is one reason that this synthetic mode is favored.

Titanostannosilicalites prepared as described above may be used directly or may be ion exchanged with a cation such as an alkali metal or alkaline earth cation. Cation exchange may affect selectivity and sometimes may counter detrimental effects of impurities but this variant is considered optional rather than essential and mandatory. Where cation exchanged material is used, exchange with an alkali metal cation, especially that of sodium and potassium, is possible. Exchange with an alkaline earth metal cation is another variant, one in which the use of magnesium and calcium is possible. The metal exchanged commonly is at a level between about 0.05 and about 0.25 weight percent based on the titanostannosilicalite.

Olefinic compounds are oxidized using principally hydrogen peroxide as the oxidizing agent in the presence of the aforedescribed catalyst under epoxidation reaction conditions. Such reaction conditions include a temperature as low as about 0° C. up to as high as about 100° C. However, where hydroxyl-containing solvents are present, as usually is the case since aqueous hydrogen peroxide is the most common peroxide source, epoxides frequently react with the hydroxylic component at temperatures above about 50° C. In such instances temperatures in the range 0°–50° C. are preferred, especially those in the 30°–45° C. interval. Epoxidation may be conducted at atmospheric pressure, although a major reason to perform the epoxidation at elevated pressure is to increase the solubility of gaseous reactants in the reaction medium. For example, where propylene is epoxidized without the use of a cosolvent increased pressure leads to an increased solubility of the propylene in aqueous solution with an increase in overall rate of propylene epoxide formation. In a greatly preferred variant epoxidation is performed in aqueous alcohols, especially alcohols having fewer than 5 carbons. We particularly prefer conducting epoxidations in aqueous methanol as the solvent system. Other water-miscible cosolvents also may be employed. For example, acetone and water-soluble ethers such as dioxane, tetrahydrofuran, and ethers of ethylene glycol and poly (ethylene glycol)—the glymes—may be fruitfully used. In another variant the feed contains from 2 up to 200 ppm of a buffer, preferably between about 5 and 20 ppm, with potassium acetate being especially useful.

Epoxidation may be performed according to our invention in either a batch or continuous mode. For example, in a batch mode the olefinic compound, either alone or in an organic solvent, is mixed with an aqueous hydrogen peroxide solution in the presence of an effective amount of our catalyst.

The amount of titanostannosilicalite used per mole of carbon—carbon double bond to be epoxidized may be as low as about 3 grams per mole. There is no theoretical limit to the maximum amount of titanostannosilicalite to be used, although as a practical matter there is no benefit from using more than about 30 grams per mole of carbon—carbon double bond. The reaction mixture is stirred well at temperatures between 0° C. up to as high as about 100° C., although in hydroxylic solvents the practical upper limit is about 80° C. The hydrogen peroxide may be present at a concentration as low as about 2 weight percent and as high as about 50 weight percent. Whether the hydrogen peroxide or the olefinic compound is present in excess depends upon the nature of the olefinic compound as well as its cost. For example, where propylene is being epoxidized, unreacted gaseous propylene may be readily recovered and recycled. In such an instance it is advantageous to have the olefinic compound in molar excess, perhaps as much as 2–5 moles per mole of hydrogen peroxide. However, where a rather expensive, or relatively unavailable, olefinic compound is being epoxidized, it may be highly advantageous to use hydrogen peroxide in molar excess, perhaps in amounts as little as 5–10% molar excess, although molar ratios of up to 5 may be employed. In general, then, the molar ratio of olefinic compound to hydrogen peroxide may range from 1:5 to 5:1.

Where the reaction is performed in a continuous mode one may employ any of the conventional process techniques currently known. These include use of a fixed bed process, a continuous stirrer tank reactor process, a radial bed reactor process, and so on. In such cases the catalyst of our invention may be used as pellets, extrudates, spheres, and the like. When our catalyst is used in such forms it is preferable to incorporate a binder for preserving and enhancing catalyst integrity. Conventional binders include silica, alumina, silica-alumina, and various clays, but since such conventional materials are well known to those skilled in the binder art no further detailed discussion will be given. The exothermicity of the epoxidation reaction and activity of our materials also requires dilution of the active molecular sieve component in the catalyst bed to a maximum of about 18 weight percent titanostannosilicalite. At this dilution the heat of reaction is readily controlled.

The following examples merely illustrate the process of our invention and are not intended to limit it in any way. Variants of the following examples may be readily envisioned by the skilled worker and are deemed to be within the scope of our invention.

EXAMPLES

Preparation of a Titanostannosilicalite: 700 g TEOS (tetraethylorthosilicate) and 57.90 g Ti(O-iPr)$_4$ were placed in a large beaker and stirred vigorously. Separately, 468.8 g TPAOH (tetrapropylammonium hydroxide) (40%) was diluted with 600 g deionized water. This solution was added in a fast dropwise fashion to the stirring alkoxides. In the first few minutes of the additions a white precipitate begins to appear, but it redissolves as more TPAOH solution is added. At the end of the addition the mixture is a clear colorless solution. This is allowed to stir 30 minutes. A solution is prepared by dissolving 11.55 g SnCl$_4$·5H$_2$O in 68 g deionized water. This is then added dropwise to the reaction mixture. At the end of this addition, the reaction mixture is still a solution. The reaction mixture is then vigorously stirred for another hour before it is placed in an autoclave with stirring capabilities. The mixture is digested for 72 hours at 150° C.

The products solids are isolated, washed with deionized water, and dried at 120° C. The dried solid is then calcined at 550° C. in air to form the catalyst. The infrared spectrum of calcined material shows a band at 962 cm-1, which is consistent with reports of framework titanium in the silicalite structure. The ultraviolet-visible spectrum shows absorbance at approximately 210 nm, which is associated with framework-incorporated titanium. Extra-framework titania, which is characterized by a broad absorbance from 285–350 nm, was absent as indicated by no significant absorbance within the aforementioned range.

X-Ray Diffraction Data. The X-ray diffraction data summarized in table 1 are typical of the titanostannosilicalites prepared and are indicative of the silicalite structure. The broad line widths are due to the small (ca. 0.1 μ) crystallite size. The results presented are for calcined material, with appreciable variation often noted between calcined and uncalcined material. The d-spacings can vary +/− 0.25 angstroms.

TABLE 1

| X-Ray Diffraction Data for a Calcined Titanostannosilicalite |||
|---|---|---|
| 2-theta (deg) | d (angstroms) | Intensity |
| 8.02 | 11.01 | vs |
| 8.93 | 9.89 | s |
| 13.31 | 6.64 | w |
| 14.03 | 6.30 | w |
| 14.92 | 5.93 | m |
| 15.63 | 5.66 | w |
| 16.02 | 5.53 | w |
| 17.85 | 4.96 | w |
| 19.39 | 4.57 | w |
| 20.97 | 4.23 | w |
| 23.27 | 3.82 | s |
| 23.88 | 3.72 | m |
| 24.08 | 3.69 | m |
| 29.44 | 3.03 | w |
| 30.12 | 2.96 | w |
| 45.32 | 1.99 | w |
| 24.56 | 3.62 | w |

X-Ray Photoelectron Spectroscopic Analysis. As evidence of the framework incorporation of tin into the titanium silicalite structure, X-ray photoelectron spectroscopy was utilized to measure the Ti/Si and Sn/Si ratio at both the surface and in the bulk of sample crystals. Sample A was prepared by tin impregnation of a titanium silicalite. A 10 gram sample of TS-1 was impregnated with an aqueous solution of SnCl$_4$. The sample was dried, then calcined at 550° C. Sample B was prepared via a precursor gel formation from titanium, tin, and silicon sources. Results are tabulated below.

TABLE 2

| X-ray Photoelectron Spectroscopic Analysis |||||
|---|---|---|---|---|
| | Ti/Si || Sn/Si ||
| Sample | surface | bulk | surface | bulk |
| A | 0.016 | 0.019 | 0.0120 | 0.0021 |
| B | 0.015 | 0.015 | 0.0030 | 0.0026 |

These data clearly show that the Sn/Si ratio differs for surface and bulk measurements in sample A, but are identical at the surface and bulk in sample B. This is convincing evidence for the presence of tin in the framework of sample B.

X-Ray Absorbtion Near Edge Spectroscopy (XANES). This analytical technique was applied to determine the local bonding geometry and oxidation state of some titanostannosilicalites. The data were collected on beamline X19A at the National Synchrotron Light Source. Brookhaven National Laboratory. The x-rays were monochromatized with an NSLS boomerang-type flat crystal monochromator with Si(111) crystals and collimated with an Al-coated glass mirror (critical energy 11 keV). The harmonic content was reduced by detuning the monochromator crystals by 30%. The XANES spectra were measured as fluorescence yield excitation spectra using a Lytle-type detector with nitrogen gas. The incident beam intensity was monitored with a split ion chamber with a constant purge of He. The incident beam size was approx. 1 mm×1 mm. The XANES of the reference compounds were measured as either electron yield spectra (using a detector manufactured by The EXAFS Co.), or as fluorescence yield spectra of material diluted to approx. 1 wt. % in BN. To minimize absorption by the air, the detector was placed close to the end of the beam pipe. All of the spectra were collected at room temperature. The monochromator was calibrated using Ti (4966.0 eV), V (5465.0 eV) and Sn (3929.0 eV) reference foils.

Spectra were processed using the BAN software package. The energy scales were established by setting the maximum of the first derivative of the XANES spectrum of the metal foils to 0.0 eV. Thus for the Ti K-edge data, 0.0 eV=4966.0 eV. The background was approximated by a least squares fit of the pre-edge region (−45 to −10 eV) and was subtracted from the spectrum. The spectra were then normalized to unity absorption by using a single point normalization well above the absorption edge. This normalization process is expected to give spectra that can be qualitatively compared only.

The Ti K-edge XANES of three Ti reference compounds were studied: anatase. $TiO_2$; barium orthotitanate. $Ba_2TiO_4$; and fresnoite. $Ba_2TiSi_2O_8$. The spectra of all three compounds have one or more prominant pre-edge absorption features before the main absorption edge itself. The spectra of barium orthotitanate and fresnoite have a single feature, whereas anatase shows a triplet. These features have been well-studied in the literature, and indeed accurate information on the local coordination environment of the Ti can be derived if both the pre-edge position and height are known [F. Farges, G. E. Brown, J. J. Rehr, *Geochim. Et Cosmo. Acta*, 60 (1996) 3023]. These features are attributed to transitions from the 1 s energy levels of Ti to the Ti 3d/O 2p molecular orbitals. A 1s to 3d transition is forbidden by dipole selection rules but becomes allowed when p-d orbital mixing occurs in a site without a center of symmetry e.g. when Ti is located in a $TiO_4$ tetrahedron. The height and position of the pre-edge feature are direct functions of the degree of p-d mixing and oxidation state. From the large body of data that has been acquired on Ti-O reference materials three main domains of height/position can be identified for 4-, 5- and 6-coordinated Ti [F. Farges et. al. *op. cit.*]. The data summarized in Table 3 are in excellent agreement with the published values.

TABLE 3

| Ti Reference Compounds | | | | |
|---|---|---|---|---|
| Compound | | Ti coordination | Pre-edge peak position (eV) | Pre-edge peak height |
| $Ba_2TiO_4$ | Barium orthotitanate | 4 | 4969.0 | 0.65 |
| $Ba_2TiSi_2O_8$ | Fresnoite | 5 | 4970.2 | 0.31 |
| $TiO_2$ | Anatase | 6 | 4971.5 | 0.17 |

The spectra of the titanostannosilicalite samples G and H are dramatically different. The spectrum from sample H shows a single intense pre-edge feature, whereas that from sample G shows a spectrum more similar to that of anatase. The position and height of the pre-edge peak from sample H indicates that the Ti is 4-fold coordinate. A spectrum fit to that of 77% anatase +23% sample H shows reasonable agreement to that of sample G. Thus, while all the Ti in sample H is 4-fold coordinate (and therefore all framework Ti), 77±5% of the Ti in sample G is present as anatase-like titanium, and is thus extra-framework. Moreover, from the ratio of the step heights of the absorption edge itself, there is 4.4 times as much Ti in sample G than in sample H.

Oxidation with Titanosilicalites and Titanostannosilicalites. Catalytic Testing. Hydrogen peroxide (40 g, 30 weight percent concentration of $H_2O_2$), 200 g methanol, and 5 g catalyst were loaded to 300 cc stainless steel autoclave. At room temperature was charged 80 g liquid propylene with nitrogen. The pressure was increased with nitrogen to 500 psi and the temperature was increased to 40/C over 30 min. The molar ratio of propylene to $H_2O_2$ under these conditions is 5; $H_2O_2$ is the limiting reagent. Liquid samples were taken at 1.3, 4 and 6 hrs. After 6 hrs the reaction was shut down and the autoclave was depressured. The remaining liquid was sampled again. This final sample is termed the "shutdown" sample.

The samples were analyzed by GC. The yield of propylene oxide is expressed as concentration of propylene oxide in the sample to the maximum theoretical concentration of propylene oxide. (Yield=|Propylene oxide|/|Propylene oxide|$_{max\ theoretical}$) The selectivity to propylene oxide is calculated as the ratio of the concentration of propylene oxide in the sample to the sum of the concentrations of propylene oxide, methoxy-propylene glycols, and propylene glycol. The batch autoclave results for the Ti-V silicalites prepared via aqueous and non-aqueous routes are shown below.

TABLE 4

| Propylene Oxidation with Various Silicalites | | | | | | | | | | |
|---|---|---|---|---|---|---|---|---|---|---|
| | | Molar Ratio in Gel | | | | Crystallization | Atomic Ratio in Sieve | | | |
| Sample | Si | Ti | Sn | $H_2O$ | TPAOH | Temp., °C. | Si/Ti | Si/Sn | Yield | Selectivity |
| A[b] | | | | | | | 47 | | 45 | 71 |
| B | 100 | 3 | 0.3 | 3760 | 33[a] | 175 | 64 | 390 | 64 | 77 |
| C | 100 | 3 | 0.3 | 3760 | 33[a] | 175 | 24 | 200 | 88 | 87 |
| D | 100 | 3 | 1 | 3015 | 33[a] | 150 | 57 | 70 | 39 | 46 |

TABLE 4-continued

Propylene Oxidation with Various Silicalites

| | Molar Ratio in Gel | | | | | Crystallization | Atomic Ratio in Sieve | | | |
|---|---|---|---|---|---|---|---|---|---|---|
| Sample | Si | Ti | Sn | $H_2O$ | TPAOH | Temp., °C. | Si/Ti | Si/Sn | Yield | Selectivity |
| E | 100 | 6 | 1 | 1400 | 32 | 100 | 144 | 836 | 51 | 91 |
| F | 100 | 6 | 1 | 3000 | 45 | 160 | 55 | 377 | 83 | 87 |
| G | 100 | 6 | 1 | 1600 | 28 | 175 | 20 | 146 | 62 | 80 |
| H | 100 | 6 | 1 | 1600 | 28 | 150 | 66 | 150 | 74 | 75 |
| I | 100 | 6 | 1 | 1600 | 28 | 125 | 80 | 364 | 66 | 76 |
| J | 100 | 6 | 1 | 1600 | 28 | 100 | 135 | 1125 | 49 | 84 |
| K | 100 | 5 | 0 | 1616 | 28 | 100 | 143 | 0 | 30 | 88 |
| L | 100 | 5 | 0 | 1616 | 28 | 125 | 63 | 0 | 47 | 89 |
| M | 100 | 5 | 0 | 1616 | 28 | 150 | 51 | 0 | 56 | 85 |
| N | 100 | 5 | 0 | 1616 | 28 | 175 | 21 | 0 | 45 | 56 |

$^a$= 142 Parts isopropyl alcohol
$^b$= Sample of TS-1 provided by PUNA National Laboratory, India.

What is claimed is:

1. A process for the epoxidation of a carbon-carbon double bond in an olefinic compound comprising reacting under epoxide-forming conditions the olefinic compound in a feedstock with a hydroperoxide in the presence of a crystalline titanostannosilicalite molecular sieve composition, where the tin and silicon are present as framework tetrahedral oxide units, said sieve having a unit empirical formula on an anhydrous basis of $(Ti_xSn_ySi_z)O_2$, where x has a value between about 0.0005 and about 0.03, y has a value between about 0.0001 and about 0.01, and $(x+y+z)=1$.

2. The process of claim 1 where epoxide-forming conditions include a temperature between about 0° C. and about 100° C.

3. The process of claim 1 where the hydroperoxide is hydrogen peroxide.

4. The process of claim 3 where the hydrogen peroxide is at a concentration from about 2 weight percent up to about 50 weight percent.

5. The process of claim 3 where the hydrogen peroxide is at a concentration between about 2 and about 15 weight percent.

6. The process of claim 5 where the hydrogen peroxide is at a concentration between about 2 and about 10 weight percent.

7. The process of claim 1 where the olefinic compound is an alkene or cycloalkene.

8. The process of claim 7 where the alkene is propylene.

9. The process of claim 7 where the cycloalkene is cyclohexene.

10. The process of claim 1 where the olefinic compound is allyl chloride.

11. The process of claim 10 where the olefinic compound is hexene-1.

12. The process of claim 1 where the olefinic compound is a carboxylic acid, a carboxylic acid anhydride, or an ester of a carboxylic acid.

13. The process of claim 12 where the carboxylic acid or an ester thereof is maleic acid, fumaric acid, esters thereof, or any mixture thereof.

14. The process of claim 1 further characterized in that the olefinic compound is reacted as a solution in an organic solvent.

15. The process of claim 1 where the crystalline titanostannosilicalite molecular sieve has an average particle size no more than about 0.5 microns.

16. The process of claim 1 where the crystalline titanostannosilicalite molecular sieve has an average particle size no more than about 0.3 microns.

17. The process of claim 1 where the feedstock contains from about 2 up to about 200 parts per million potassium cations.

* * * * *

UNITED STATES PATENT AND TRADEMARK OFFICE
CERTIFICATE OF CORRECTION

PATENT NO. : 5,780,654
DATED : July 14, 1998
INVENTOR(S) : NEMETH, et al.

It is certified that error appears in the above-identified patent and that said Letters Patent is hereby corrected as shown below:

In Claim 1, column 11, line 26, insert after tin and before and --, titanium--.

Signed and Sealed this

Fifteenth Day of September, 1998

Attest:

BRUCE LEHMAN

*Attesting Officer*       *Commissioner of Patents and Trademarks*